US006966047B1

(12) United States Patent
Glasser

(10) Patent No.: US 6,966,047 B1
(45) Date of Patent: Nov. 15, 2005

(54) CAPTURING DESIGNER INTENT IN RETICLE INSPECTION

(75) Inventor: Lance A. Glasser, Saratoga, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 61 days.

(21) Appl. No.: 10/139,109

(22) Filed: May 2, 2002

Related U.S. Application Data

(60) Provisional application No. 60/371,647, filed on Apr. 9, 2002.

(51) Int. Cl.$^7$ .......................... G06F 17/50; G06K 9/00
(52) U.S. Cl. .................... 716/19; 382/144; 382/149
(58) Field of Search .................... 716/19; 382/144, 382/149

(56) References Cited

U.S. PATENT DOCUMENTS

| | | | |
|---|---|---|---|
| 4,532,650 A | 7/1985 | Wihl et al. | 382/144 |
| 4,717,644 A | 1/1988 | Jones et al. | 430/296 |
| 4,758,094 A | 7/1988 | Wihl et al. | 356/394 |
| 4,989,255 A | 1/1991 | Manns et al. | 382/145 |
| 5,097,422 A | 3/1992 | Corbin, II et al. | 716/8 |
| 5,113,451 A | 5/1992 | Chapman et al. | 382/145 |
| 5,150,308 A | 9/1992 | Hooper et al. | 716/18 |
| 5,230,075 A | 7/1993 | Premerlani et al. | 707/1 |
| 5,267,175 A | 11/1993 | Hooper | 716/18 |
| 5,287,290 A | 2/1994 | Tabara et al. | 716/5 |
| 5,416,722 A | 5/1995 | Edwards | 716/21 |
| 5,483,461 A | 1/1996 | Lee et al. | 716/14 |
| 5,551,014 A | 8/1996 | Yoshida et al. | 716/11 |
| 5,619,429 A | 4/1997 | Aloni et al. | 700/279 |
| 5,623,417 A | 4/1997 | Iwasaki et al. | 716/18 |
| 5,625,568 A | 4/1997 | Edwards et al. | 716/2 |
| 5,804,340 A | 9/1998 | Garza et al. | 430/5 |
| 5,994,030 A | 11/1999 | Sugihara et al. | 514/553 |
| 6,009,251 A | 12/1999 | Ho et al. | 716/5 |
| 6,097,884 A | 8/2000 | Sugasawara | 716/4 |
| 6,282,309 B1 | 8/2001 | Emery | 382/145 |
| 6,449,749 B1 * | 9/2002 | Stine | 716/4 |
| 6,483,937 B1 * | 11/2002 | Samuels | 382/144 |
| 6,529,621 B1 * | 3/2003 | Glasser et al. | 382/144 |

(Continued)

FOREIGN PATENT DOCUMENTS

JP      10 242038 A      11/1998      ......... H01L 21/027

(Continued)

OTHER PUBLICATIONS

P. Depesa et al., "Automated Critical Dimension and Registration Communication," Proceedings of SPIE, The International Society for Optical Engineering, vol. 1604, pp. 26-33, 1991.

(Continued)

Primary Examiner—A. M. Thompson
(74) Attorney, Agent, or Firm—Beyer, Weaver & Thomas, LLP.

(57) ABSTRACT

A method of inspecting a reticle for defining a circuit layer pattern. First, the circuit layer pattern is analyzed to obtain a circuit characterization, and then, an area of the reticle is categorized into a first region and a second region based on the circuit characterization. A test reticle image of the reticle and a baseline representation containing an expected pattern of the test reticle image are provided. The first region of the test reticle image is compared to the first region of the baseline representation by a first analysis, and the second region of the test reticle image is compared to the second region of the baseline representation by a second analysis. The first analysis differs from the second analysis and this difference is based on difference in the circuit characterization of the first and second regions.

5 Claims, 10 Drawing Sheets

U.S. PATENT DOCUMENTS

| | | | |
|---|---|---|---|
| 6,748,103 B2 * | 6/2004 | Glasser et al. | 382/149 |
| 2003/0086081 A1 * | 5/2003 | Lehman | 356/237.1 |
| 2003/0142860 A1 * | 7/2003 | Glasser et al. | 382/144 |

FOREIGN PATENT DOCUMENTS

| WO | WO00/36525 | 6/2000 |
|---|---|---|

OTHER PUBLICATIONS

Barry Simon, Javier Prado, and Larry Day, "Software Tools For Analysis of Water Sort Yield Data", 1987 Test Conference, paper 28.1, presented by Motorola, Inc., Memory Products Division, Austin, Texas, 10 pages.

* cited by examiner

| | Layer #1 | Location | Tag |
|---|---|---|---|
| Cell A = | Figure 1 | $(x,y)_1(x,y)_2$ | 1 |
| | Figure 2 | $(x,y)_1(x,y)_2$ | 0 |
| | Figure 3 | $(x,y)_1(x,y)_2$ | 1 |
| | Figure 4 | $(x,y)_1(x,y)_2$ | 0 |
| Cell B = | Cell A | $(x,y)$ | - |
| | Cell A | $(x,y)$ | - |
| | Cell A | $(x,y)$ | - |
| | Cell B | $(x,y)$ | - |
| | Cell B | $(x,y)$ | - |
| | Cell B | $(x,y)$ | - |

| | Layer #1 | Location | Tag |
|---|---|---|---|
| Cell A = | Figure 1 | $(x,y)_1(x,y)_2$ | gate |
| | Figure 2 | $(x,y)_1(x,y)_2$ | - |
| | Figure 3 | $(x,y)_1(x,y)_2$ | contact |
| | Figure 4 | $(x,y)_1(x,y)_2$ | - |
| Cell B = | Cell A | $(x,y)$ | - |
| | Cell A | $(x,y)$ | - |
| | Cell A | $(x,y)$ | - |
| | Cell B | $(x,y)$ | - |
| | Cell B | $(x,y)$ | - |
| | Cell B | $(x,y)$ | - |

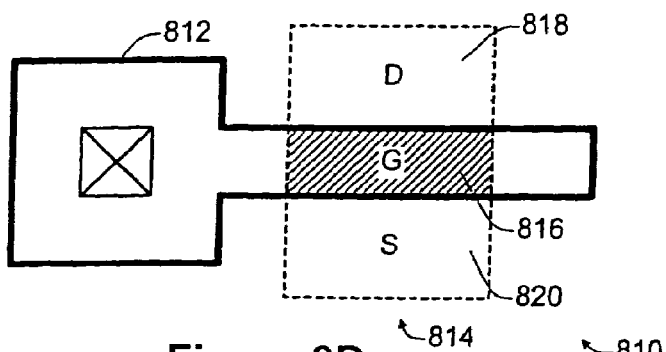
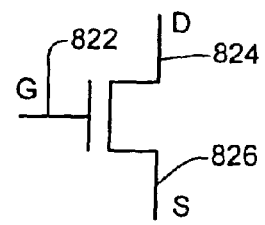
Figure 8D    Figure 8E
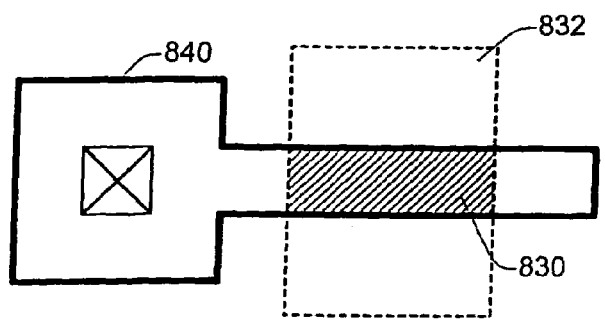
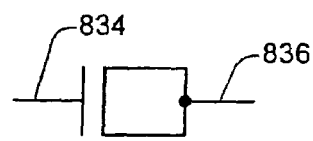
Figure 8F    Figure 8G
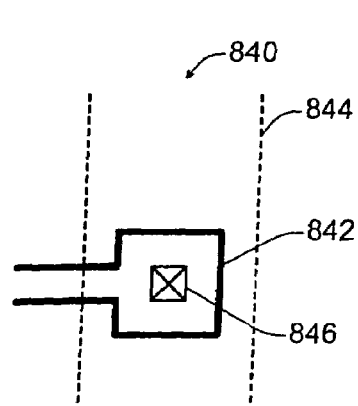
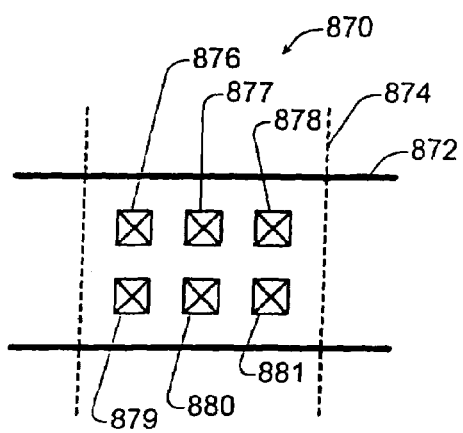
Figure 8H    Figure 8I

CAPTURING DESIGNER INTENT IN RETICLE INSPECTION

CROSS-REFERENCE TO RELATED APPLICATIONS

This application claims priority under 35 U.S.C. 119(e) from U.S. Provisional Patent Application No. 60/371,647 for "CAPTURING DESIGNER INTENT IN RETICLE INSPECTION" (Glasser) filed on Apr. 9, 2002, which is incorporated herein by reference for all purposes.

BACKGROUND OF THE INVENTION

The present invention relates generally to integrated circuit design and fabrication systems. More specifically, the invention relates to mechanisms for generating and inspecting reticles and other types of samples.

Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout typically includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles.

A reticle or photomask is an optical element containing transparent and opaque, semi-transparent, and phase shifting regions which together define the pattern of coplanar features in an electronic device such as an integrated circuit. Reticles are used during photolithography to define specified regions of a semiconductor wafer for etching, ion implantation, or other fabrication process. For many modern integrated circuit designs, an optical reticle's features are between about 1 and about 10 times larger than the corresponding features on the wafer. For other exposure systems (e.g., x-ray, e-beam, and extreme ultraviolet), a similar range of reduction ratios also applies.

Optical reticles are typically made from a transparent medium such as a borosilicate glass or quartz plate on which is deposited an opaque and/or semi-opaque layer of chromium or other suitable material. However, other mask technologies are employed for direct e-beam exposure (e.g., stencil masks), x-ray exposure (e.g., absorber masks), etc. The reticle pattern may be created by a laser or an e-beam direct write technique, for example, both of which are widely used in the art.

After fabrication of each reticle or group of reticles, each reticle is typically inspected by illuminating it with light emanating from a controlled illuminator. An optical image of the reticle is constructed based on the portion of the light reflected, transmitted, or otherwise directed to a light sensor. Such inspection techniques and apparatus are well known in the art and are embodied in various commercial products such as many of those available from KLA-Tencor Corporation of San Jose, Calif.

During a conventional inspection process, the optical image of the reticle is typically compared to a baseline image. The baseline image is either generated from the circuit pattern data or from an adjacent die on the reticle itself. Either way, the optical image features are analyzed and compared with corresponding features of the baseline image. Each feature difference is then compared against at least one threshold value. If the optical image feature varies from the baseline feature by more than the predetermined threshold, a defect is defined.

Although conventional reticle inspections provide adequate levels of detection accuracy for some applications, other applications require a higher sensitivity or lower threshold value (for identifying defects) while other applications require less stringent, higher threshold levels. Also, particular structures on the reticle may require a first type of inspection algorithm, while other types of structures may require a different type of inspection algorithm.

For example, critical features of an integrated circuit typically include gate widths of the semiconductor transistor devices. That is, a gate width on the reticle needs to produce a corresponding gate width on the circuit pattern within a relatively small margin of error in order for the fabricated IC device to function properly. If the threshold is set too high, these critical gate areas are not checked adequately enough. Conversely, other features, such as the widths of the interconnections between gate areas, do not affect the function of the integrated circuit as much as the gate area width and, thus, do not need to be inspected as stringently as other features, such as gate width. If the threshold is set too low, too many of these noncritical features may be defined as defects such that the inspection results are difficult to interpret and/or computational resources are overloaded.

In sum, conventional techniques only use information available from geometry of single layer. Also, conventional inspection systems waste valuable resources by inspecting regions of the reticle too stringently, and not inspecting other regions stringently enough. In other words, the above described inspection system fails to reliably detect defects within critical areas and inefficiently inspects noncritical regions where somewhat larger defects will not present a problem. Conventional inspection systems and techniques are unable to distinguish between different types of features, such as critical and noncritical areas of the reticle. Put in another way, conventional design documentation (e.g., electronic reticle or integrated circuit information) fails to adequately transmit the IC designer's intent regarding the circuit tolerance and resulting IC device dimensions to reticle writer systems, reticle inspection systems, and ultimately wafer inspection systems.

What is needed is improved IC documentation and apparatus for more efficiently and reliably writing and inspecting reticles and wafers.

SUMMARY OF THE INVENTION

The present invention addresses the needs described above by conveying the circuit designer's intent regarding an inspection/fabrication criterion. For example, an inspection criterion may specify how a portion of the reticle is to be inspected, and a fabrication criterion may indicate how a portion of the reticle is to be fabricated. Specifically, the inspection/fabrication criterion is conveyed by associating one or more flags (or no flag) with specific portion(s) of the design data. The presence or absence of a flag generally indicates a characteristic, such as functionality, of the flagged or non-flagged design data portion after it is fabricated (referred to herein as a "test portion"). The characteristic may indicate:

(i) whether the test portion functions as an active transistor, or a decoupling capacitor;

(ii) whether a test portion includes only a single via hole to connect two layers, or includes a plurality of via holes to connect the two layers;

(iii) whether a test portion is an area for an active element, or an area for a CMP (chemical mechanical polishing) dummy element; or (iv) whether a test portion includes a critical path or not.

An inspection/fabrication system according to one embodiment of the present invention is capable of modifying an inspection/fabrication criterion based on the flag indicating a circuit characterization type which represents, for example, the above-identified four categories (i)–(iv).

According to a specific embodiment of the present invention, a circuit design for use with EDA (electronic design automation) tools contains an electronic representation of a layout pattern. The layout pattern includes a first layout region having a first flag, and a second layout region having a second flag or no flag. The first flag indicates that a first procedure region of a reticle or an integrated circuit has a first circuit characterization type and is thereby subject to a first inspection or fabrication procedure. The second flag or absence of a flag of the second layout region indicates that a second procedure region of the reticle or integrated circuit has a second circuit characterization type and is thereby subject to a second inspection or fabrication procedure. The second inspection or fabrication procedure differs from the first inspection or fabrication procedure.

In one embodiment, the first circuit characterization type is an active transistor, and the second circuit characterization type is a decoupling transistor. Alternatively, the first circuit characterization type is a single via hole area, and the second circuit characterization type is a multiple via hole area. In another embodiment, the first circuit characterization type is an active element, and the second circuit characterization type is a dummy element. In still another embodiment, the first circuit characterization type is an element which is included in a critical path, and the second circuit characterization type is an element which is not included in the critical path.

Another embodiment provides a method of inspecting a reticle for defining a circuit layer pattern. Such a method includes analyzing the circuit layer pattern to obtain a circuit characterization. Then, an area of the reticle is categorized into a first region and a second region based on the circuit characterization. The reticle is subject to one of different sets of analysis based on whether the portion under the analysis is the first region or the second region.

Still another embodiment provides a method of generating a layout pattern with a flag for an integrated circuit device. In the method, first, a schematic representation and/or a high level description of the integrated circuit device is generated. Then, the layout pattern is generated based on the schematic representation and/or the high level description. Finally, the flag is added to the layout pattern based on a circuit characterization of the layout pattern.

A further understanding of the nature and advantages of the present invention may be realized by reference to the remaining portions of the specification and the drawings.

BRIEF DESCRIPTION OF THE DRAWING

The invention, together with further objects and advantages thereof, may best be understood by reference to the following description taken in conjunction with the accompanying drawings in which:

FIG. 8D is a diagram of two representations of layout patterns used to fabricate a transistor according to one embodiment of the present invention.

FIG. 8E is a schematic diagram of an equivalent circuit of the transistor shown in FIG. 8D.

FIG. 8F is a diagram of two representations of layout patterns used to fabricate a decoupling capacitor according to one embodiment of the present invention.

FIG. 8G is a schematic diagram of an equivalent circuit of the decoupling capacitor shown in FIG. 8F.

FIG. 8H is a diagram of two representations of layout patterns used to fabricate via holes which are subject to more stringent inspection/fabrication according to one embodiment of the present invention.

FIG. 8I is a diagram of two representations of layout patterns used to fabricate via holes which are subject to less stringent inspection/fabrication according to one embodiment of the present invention.

DETAILED DESCRIPTION OF SPECIFIC EMBODIMENTS

Various embodiments of the present invention will now be described in detail with reference to the drawings, wherein like elements are referred to with like reference labels throughout.

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
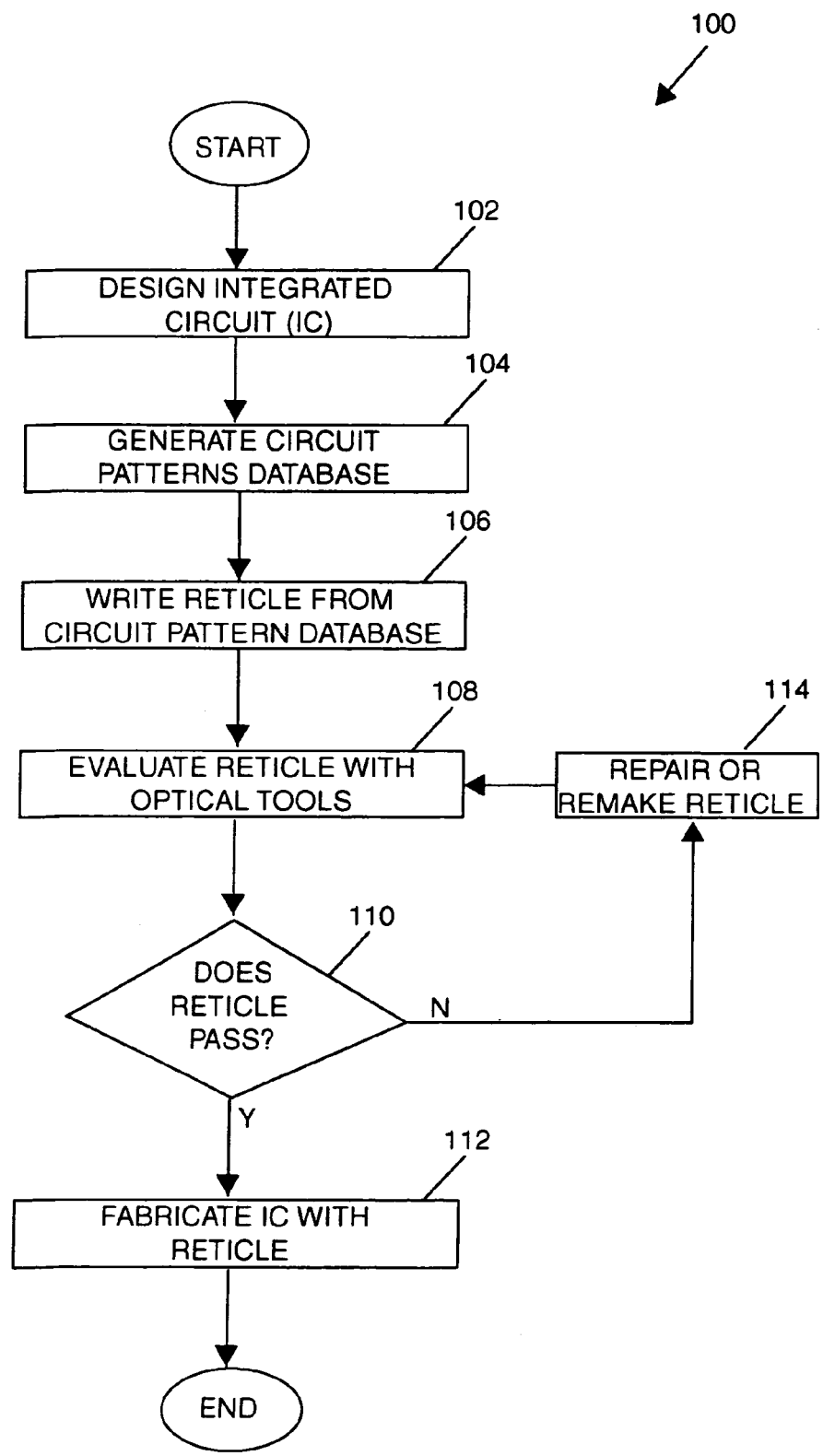
FIG. 1 is a flowchart illustrating an integrated circuit design process in accordance with one embodiment of the present invention.

FIG. 1 is a flowchart illustrating an integrated circuit design process 100 in accordance with one embodiment of the present invention. Initially, in operation 102, an integrated circuit (IC) device is designed using any suitable design techniques. For example, an IC designer may use preexisting schematic library blocks to form the IC device using, for example, electronic design automation (EDA) tools. In some cases, the IC designer may create the IC device or part of the IC device from scratch with the aid of any suitable design system, such as conventional computer aided design (CAD) tools. For example, the IC designer may use a schematic CAD tool to plan the logic diagrams for a particular IC device. Still further, the IC designer may write a description of the IC device or portions of the IC device with the aid of a hardware design language, such as VHDL.

Next, in operation 104 the IC designer generates a circuit pattern database (commonly referred to as a "layout") from the IC design in operation 102. The circuit pattern database is composed of a plurality of electronic representations of layout patterns for IC layers which are later converted into a plurality of reticles. The reticles are then used to fabricate a plurality of physical layers of an IC device. Each physical layer of the fabricated IC device corresponds to one of the reticles and an associated one of the electronic representations of the circuit pattern database. For example, one electronic representation may correspond to a diffusion pattern on a silicon substrate, another to a gate oxide pattern, another to a gate polysilicon pattern, another to a contact pattern on an interlayer dielectric, another to a line pattern on a metallization layer, and so on. When double exposure techniques are used in, for example, alternating PSM (phase shift mask), each physical layer of the fabricated IC device corresponds to a plurality of the reticles and associated ones of the electronic representations of the circuit pattern database. Each electronic representation is composed of a plurality of polygons or other shapes (herein, referred to as "figures"), which together define the reticle pattern.

The circuit pattern database may be generated using any suitable technique, for example, by using EDA or CAD tools. For example, the IC designer may manually lay out the circuit patterns for the IC device with or without preexisting library cells. Alternatively, a synthesis tool may automatically create circuit patterns for the IC device from scratch or by piecing together preexisting library cells.

In this invention, the circuit pattern database may include flagged portions of particular electronic representations that will be used to inform an inspection system to inspect corresponding portions of the reticle and/or fabricated IC device according to a special inspection process. The flagged portions may also be used to inform a fabrication system to fabricate corresponding portions of the reticle and/or IC device according to a special fabrication process. Mechanisms for flagging portions of the database and using such flagged portions to inspect or fabricate a reticle or IC device are further described below.

According to various embodiments of the present invention, existence of a flag (or non-existence of a flag in some cases) with respect to a particular portion of the circuit pattern or layout can indicate a "circuit characterization type" for such portion after it is fabricated (a "test portion"). The circuit characterization type may indicate, for example, (i) whether the test portion functions as a gate of an active transistor, (ii) whether the test portion includes only one single via hole to connect two layers, (iii) whether the test portion is an area for CMP (chemical mechanical polishing) dummy elements, or (iv) whether the test portion includes a critical path. Such a flag (or absence of a flag) which corresponds to, for example, one of the above four categories (i)–(iv) reflects the circuit designer's intent to inspect/fabricate a reticle based on a more stringent criterion for a more critical part of circuitry, or based on a less stringent criterion for a less critical part of the circuitry. In other words, the flag (or absence of a flag) by indicating a particular circuit characterization also indicates a particular type of inspection or fabrication procedure. Several examples of different circuit characterizations are described further below with respect to FIGS. 8A through 8I.

The flag may be added to the circuit pattern database. Alternatively, the flag may be stored separately from the circuit pattern database, and then later may be referred by the circuit pattern database for determining the stringency of an inspection/fabrication criterion. In this specification, the term "inspection/fabrication" means inspection and/or fabrication of a reticle or an IC (integrated circuit).

According to one embodiment of the present invention, an inspection/fabrication system first analyzes the circuit designed in operation 102 and/or the circuit pattern database generated in operation 104 to obtain a particular circuit characterization of a reticle or integrated circuit. Then, the system categorizes an area of the reticle or integrated circuit into two or more regions based on the circuit characterization. Subsequently, the system inspects and/or fabricates the area by one of a plurality of different inspection/fabrication procedures based on the category of the area in operation 108 or later.

After the circuit pattern database is generated, the circuit pattern database is used to produce a plurality of reticles in operation 106. The reticles may be produced by any suitable pattern generator or reticle writer equipment, such as a MEBES 4500, commercially available from ETEC of Hayward, Calif.

Each reticle corresponds to one or more electronic representation(s) from the circuit pattern database. A reticle is then inspected in operation 108, and it is determined whether the reticle passes inspection in operation 110. If the reticle passes inspection, the reticle may then be used to fabricate a physical layer of the IC device in operation 112. However, if the reticle does not pass inspection, the reticle is either repaired or remade in operation 114, and the new reticle is inspected in operation 108. Operations 106 through 112 are implemented for each electronic representation of the circuit pattern database.

The present invention may be implemented on any suitable inspection tools. For example, a TeraStar SLF 77 Reticle Inspection Tool, commercially available from KLA-Tencor of San Jose, Calif., may be employed. One embodiment of an inspection system is described below in reference to FIG. 9. The present invention may also be implemented on any suitable reticle fabrication tools. Such reticle fabrication tools are described in, for example, U.S. Pat. Nos. 4,532,650; and 4,758,094 (issued to Wihl et al. and assigned to the assignee of this invention), both of which are incorporated herein by reference for all purposes.

At least one of the electronic representations of the circuit pattern database will include one or more flagged critical regions and other nonflagged normal regions. The flagged region(s) will later be used to indicate that corresponding critical region(s) of the reticle or of the fabricated IC device requires a special inspection or fabrication procedure. The flagged regions may be flagged with different types of flags, and each flag type may correspond to different types of critical regions. For example, a first flag may indicate a gate region, while a second flag indicates a critical delay path. Alternatively, the different flags may each indicate different types of special and normal regions. For example, a first type of flag may correspond to a first type of critical region which requires a special or more stringent inspection; a second type of flag may correspond to a normal region which requires a normal or less stringent inspection; and a third flag may correspond to a second type of critical region.

In some embodiments, logical combination (for example, "AND," "OR," "NOR," and the like) of a plurality of flagged regions indicates a special or more stringent inspection. For example, suppose that there are two flagged regions F1 and F2. A special inspection may be performed based on logical combination (e.g., "AND") of the flags F1 and F2. Stated differently, in such a case, the special inspection is applied to an area where the two flagged regions F1 and F2 are overlapped.

The flagged region(s) may be flagged by any suitable technique for distinguishing the flagged region(s) from other regions of the layer. For example, an electronic representation of a given layer may contain specific flags or tags on certain ones of the "figures" making up that representation. In another embodiment, a specific layer designation may be used to identify or flag the critical region(s). In other words, two layer types are used together to represent the same circuit layer representation. (The layer type containing the flagged regions is sometimes referred to herein as a "shadow representation." The other layer type is sometimes referred to herein as a "base representation.")

Both the shadow and base representation may be used to form the same reticle, as well as for inspecting the fabricated reticle. Alternatively, an electronic representation may include multiple different shadow representations for flagging different types of critical regions on the same reticle. For example, one shadow representation may flag regions to be inspected with a high stringency threshold level or sensitivity level, while another may flag regions to be inspected with a special algorithm. Alternatively, noncritical regions may be flagged to indicate that the corresponding flagged regions are to be inspected with a low stringency threshold level, as compared to the normal regions.

Figure 2:
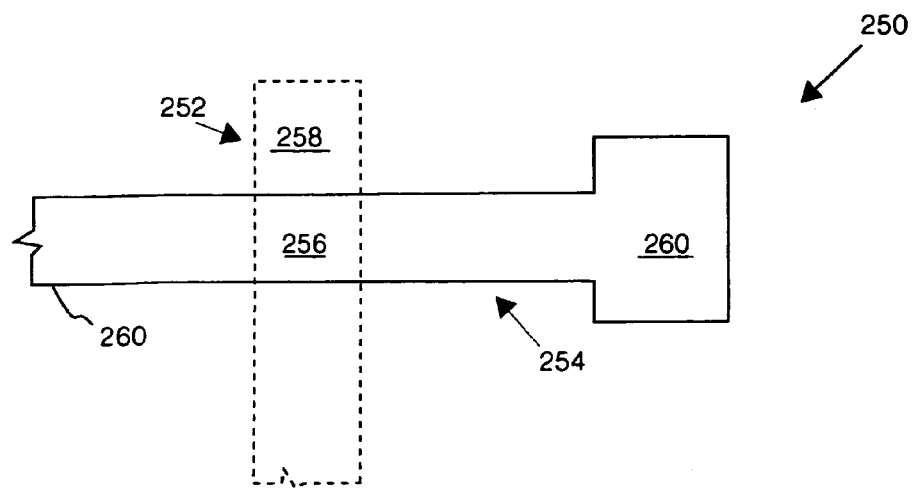
FIG. 2 is a diagram of two representations of layout patterns used to fabricate a transistor in accordance with one embodiment of the present invention.

FIG. 2 is a diagram of two representations of layout patterns used to fabricate a transistor. Together, the two representations provide a transistor representation 250 in accordance with one embodiment of the present invention. As shown, the transistor representation 250 includes (i) a poly layer representation 254 representing a polysilicon layer of the transistor, and (ii) an active area representation 252 representing the layout of an active area on a semiconductor substrate. The poly layer representation 254 provides the pattern of the polysilicon layer including a gate area of the transistor 250. The two representations of layout patterns illustrated in FIG. 2 may be expressed and stored in any suitable electronic format.

The active area layout pattern is indicated by a dotted boundary in representation 252. Residing within the dotted boundary is a diffusion region 258. It contains no critical regions and so has no flagged regions in this example. The polysilicon layout pattern is indicated by a solid boundary in representation 254. Residing within the solid boundary is a polysilicon strip 260. It contains a flagged critical region 256 at its gate electrode. In poly level representation 254, the critical region is defined by the intersection of active region 258 (from the active area representation) and polysilicon strip 260. Thus, poly representation 254 includes both a critical region 256 and a normal region including all of region 260 or at least the portions of 260 lying outside of critical region 256.

The flagged region may be used to perform enhanced inspections and/or fabrication procedures for the reticle and/or fabricated IC device. For example, although the flagged critical region and unflagged regions may both be used to make the polysilicon reticle, the flagged critical region may also be used to indicate that the corresponding critical region of the reticle may be subject to an enhanced inspection, such as a more stringent threshold. By way of another example, the flagged critical region may be used to indicate the corresponding critical region of the reticle may be subject to enhanced reticle fabrication procedures, such as using a relatively narrow electron beam to write the critical region of the reticle.

Any suitable technique may be implemented for distinguishing the normal and critical regions. Two examples will now be provided to illustrate the range of options. One way to flag the critical regions is to use one or more shadow representation(s). Each shadow representation may flag one or more specific critical region(s) of a layout pattern for a level of the integrated circuit design under consideration.

In addition to the shadow representation(s), the electronic representation for a layer of a circuit design may include a base representation containing the entire pattern (or at least those portions of the pattern outside the flagged region(s) in the shadow layer) of the layer under consideration. If the base representation includes the entire pattern, it may be used by itself to fabricate the reticle, while the shadow representation is merely used to indicate a critical region of the reticle that requires an enhanced inspection or fabrication. Thus, the base representation may be provided to the pattern generator or reticle writer so that reticles may be fabricated from the base representation, while the shadow representation(s) are passed through to the inspection or fabrication equipment so that the reticles or fabricated IC devices may be inspected based on the shadow representation(s). Alternatively, the shadow representation(s) may also be used to fabricate the associated critical regions of the reticle (or possibly the IC device). The shadow layers may also be retained at the fabrication equipment and used to set fabrication conditions during fabrication of the reticle or IC device.

More than one type of shadow representation may be used to indicate different types of inspection or fabrication procedures. For example, a set of shadow regions may be used to flag different regions of the reticle that require different inspection thresholds. By way of another example, the shadow regions may be used to flag different regions of the reticle that require qualitatively different inspection procedures, such as checking the region's area size or average width, as compared to merely checking the region's edge position.

Figure 3:
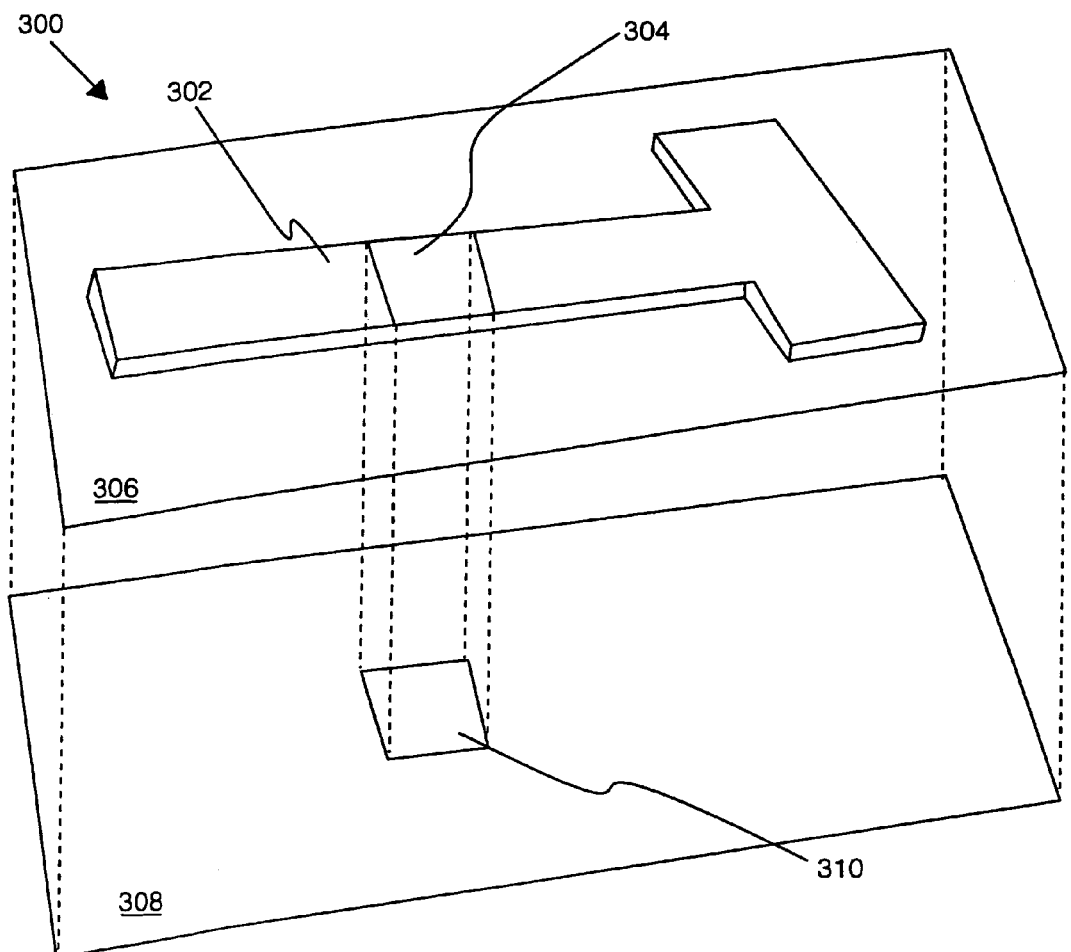
FIG. 3 is a diagram of a portion of a circuit pattern database having a base layer representation and a shadow representation in accordance with one embodiment of the present invention.

Following from the example of FIG. 2, FIG. 3 is a diagram of a portion of a circuit pattern database 300 having a base representation 306 and a shadow representation 308. Together representations 306 and 308 may denote a polysilicon layer of a transistor. In one embodiment, the base representation may be used to fabricate a reticle, while the shadow representation is not used to fabricate a reticle. Instead, the shadow representation may only be used to inspect the reticle or fabricated IC device or to fabricate the IC device. Alternatively, both the base and shadow representations may be used to fabricate the reticle. In this case, the critical regions of the shadow representation specify a special fabrication procedure (e.g., enhanced resolution by using narrower electron beams) while the base representation generally specifies a normal resolution fabrication procedure.

For inspection, the shadow representation may be used alone or in conjunction with the base representation. When both representations are used, the base representation will be provided to an inspection system to specify those regions of the reticle or wafer subject to a normal inspection procedure. The shadow representation, in contrast, will tell the inspection system which regions of the reticle or wafer require special inspection. When the shadow representation is used alone, the inspection system may inspect only those regions provided in the shadow representation (which includes at least the critical regions). Alternatively, the shadow region may be used to indicate areas requiring reduced sensitivity or no inspection at all.

In the example shown, the base representation 306 defines the pattern of a polysilicon strip 302 that includes a critical portion 304 that is flagged as region 310 in underlying shadow representation 308. That is, critical portions are flagged by adjacent shadow representations. As described above, the shadow representation may then be used to perform special inspections and/or fabrication procedures for the reticle and/or fabricated IC device. Note that when a shadow representation is used, the critical region may not need to be flagged in the base representation.

The base and shadow representation may take any convenient form readable by inspection or fabrication systems (or computers controlling such systems). Preferably, they take the form of files or other suitable machine readable data containing a list of figures (shapes or polygons) and their associated positions in a reticle or die layout. Various standard formats for such geometric layouts are available and widely used.

Another technique for flagging critical regions of an electronic representation of circuit pattern layout for a particular layer involves providing a modified base or standard representation of the layer. This embodiment does not rely on a shadow representation. In this embodiment, a file or database table for the circuit layer under consideration contains a list of figures defining the pattern layout and an associated flag for at least those figures comprising a critical region.

Figures 4, 5A:
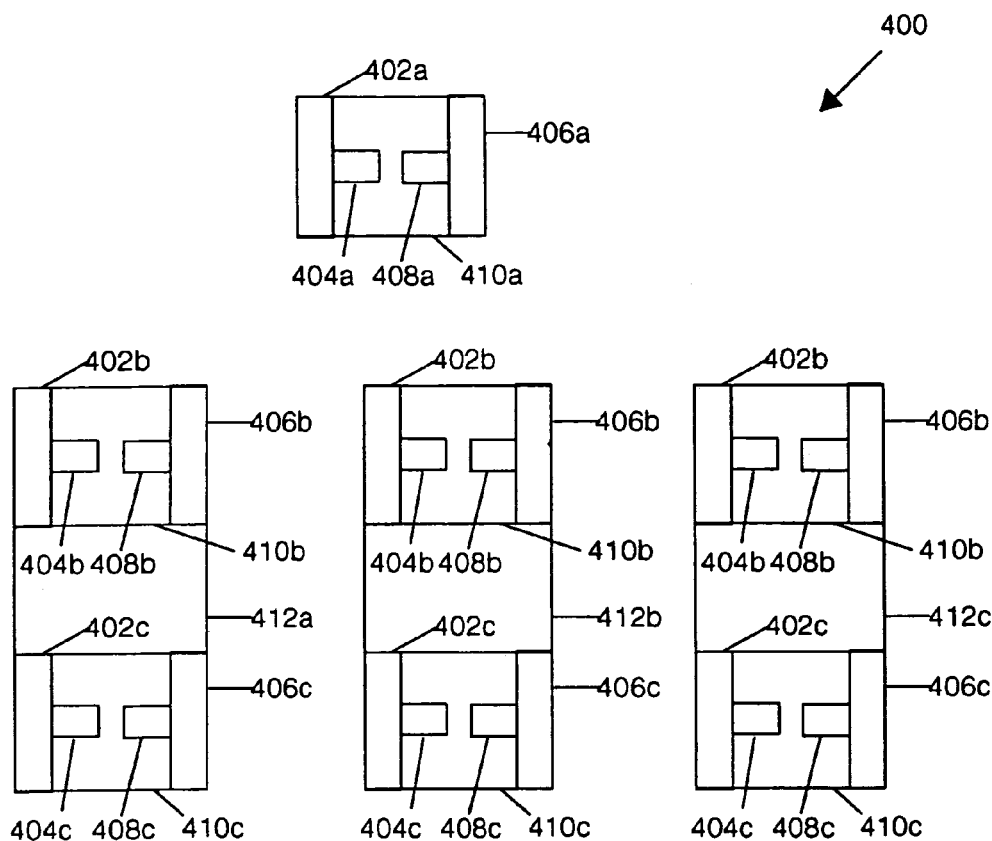
FIG. 4 is a diagrammatic representation of a circuit pattern layout in accordance with one embodiment of the present invention.
FIGS. 5A through 5C are corresponding database structures that represent the circuit pattern layout of FIG. 4 in accordance with three embodiments of the present invention.
Figure 5B:
Figure 5C:

Any suitable database structure may be implemented for the circuit pattern database of the present invention. FIG. 4 is a diagrammatic representation of a circuit pattern layout 400, and FIGS. 5A through 5C are corresponding database structures that represents the circuit pattern layout 400 of FIG. 4 in accordance with three embodiments of the present invention. A circuit pattern layout (such as that depicted in FIG. 4) may be provided as a reusable library cell for use with EDA tools, an original design custom made for a particular integrated circuit, or any other electronic representation used to depict layers in an integrated circuit design. Although only one layer is represented in the databases of FIGS. 5A through 5C, of course, the database may include the entire set of layers that correspond to all physical layers of a particular IC device.

As shown, the circuit pattern 400 includes a plurality of cell A's 410. Each cell A 410 includes a plurality of figures. As mentioned above, figures may be polygons or other shapes that when depicted together form an IC layer's pattern representation. For example, cell 410a includes figures 402a, 404a, 406a, and 408a. Each layer and cell may have one or more figures. Together these figures may define the patterning of a polysilicon layer at a specific location on an integrated circuit. Alternatively, they may define the patterning of diffusions in a substrate, a metallization layer, etc. The circuit pattern 400 also includes a plurality of cell B's 412 that are each composed of two cell A's 410. Each figure may also be flagged and associated with a particular tag or flag as shown in FIGS. 5A through 5C.

The database structures may be organized in any suitable form. For example, the database structures may be in the form of a hierarchical list of figures and cells. As shown in FIG. 5A, the database 500 for a single layer ("layer #1") of the circuit design includes a cell A definition 502, a cell B definition 504, and a listing of cells 506. The cell A definition 502 includes four figures (FIGS. 1 through 4). Each figure has a set of coordinates that denote the sizes and position of each figure within a cell A. The cell B definition 504 includes two cell A's and their respective relative positions. The listing of cells 506 represent the cells of FIG. 4. Thus, the listing 506 includes a cell A that corresponds to the cell A 410a and three cell B's that correspond to the three cell B's 412a through 412c.

Each figure is associated with a particular tag that indicates a type of inspection or fabrication procedure. Any suitable tag for distinguishing procedure types may be implemented. For example, each tag may indicate one of a plurality different threshold values for inspecting the corresponding reticle portions. In other words, the tag is related to how stringently the associated figure is to be inspected.

As shown in FIG. 5A, a tag may represent one of a plurality of threshold values, such as a "1" value which indicates a highest threshold, a "2" value which indicates a medium threshold, or a "3" which indicates a lowest threshold. Alternatively, as shown in FIG. 5B, a tag may simply indicate whether or not to perform an enhanced inspection for the particular figure. For example, the tag is either a "1" or "0" value.

By way of a final example, as shown in FIG. 5C, a tag may indicate a particular attribute of the associated critical area of the reticle. Areas with gate attributes may be inspected with gate specific algorithm sets. The tag "gate" may indicate that the associated area functions as a gate, and thus, an enhanced inspection for transistor gates is to be performed on FIG. 1. The enhanced inspection for gates may include, for example, checking the average width or length of FIG. 1. The tag "contact" may indicate that an enhanced inspection procedure for contacts is to be performed on FIG. 3. The enhanced inspection procedure may be especially applicable to checking contacts. For example, the special inspection procedure for contacts may include checking the area of the contact (FIG. 3).

The above described tags may facilitate inspection of reticles, as well as the fabricated IC device. For example, the flags may be used to select a particular inspection algorithm or to select the stringency level (e.g., threshold level) of the inspection for a particular region of the reticle and/or IC device. Additionally, the tags may facilitate fabrication of such reticles and/or IC devices. For example, the flagged regions may be used to indicate that special attention and care is to be given while fabricating the corresponding critical regions of the reticle and/or IC device.

Figure 6:
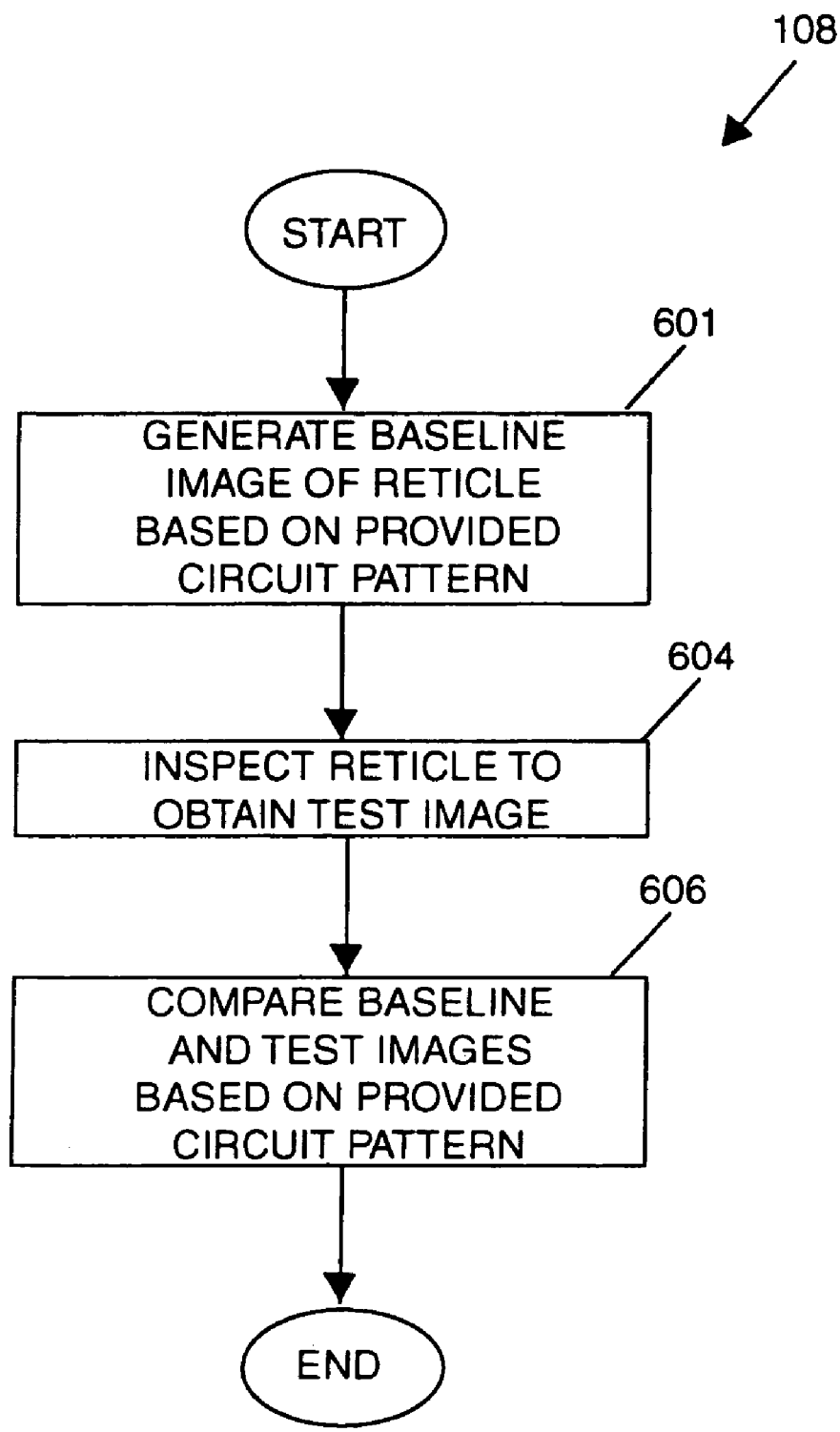
FIG. 6 is a flowchart illustrating the operation of FIG. 1 of inspecting and evaluating the fabricated reticle in accordance with one embodiment of the present invention.

FIG. 6 is a flowchart illustrating the operation 108 of FIG. 1 of inspecting and evaluating the fabricated reticle in accordance with one embodiment of the present invention. Initially, in operation 601 a baseline image of the reticle may be generated or "rendered" from the provided circuit pattern database. The baseline image may be generated in any suitable manner, such as by merely directly converting the contents of the circuit pattern database into an image. Alternatively, the circuit pattern database may be rendered by simulating fabrication results from making a reticle that perfectly matches the circuit pattern database. For example, the corners of a circuit pattern in the baseline image may be rounded to account for corner rounding that commonly occurs during fabrication of a reticle. The baseline image may also include simulated optical effects from retrieving an optical image of the simulated reticle. Such optical effects are necessarily encountered when an optical inspection technique is used to evaluate a reticle. Additionally, a vendor may provide the end user of the reticle, e.g. a fabrication facility, with the baseline image of the reticle and perform the above described steps of baseline generation phase 601.

Alternatively, the baseline image may be generated from an adjacent die of the reticle in a die-to-die inspection approach. In this approach, the images of two supposedly identical patterns on a reticle are generated, one for a baseline image and one for a test image described below. Note that many reticles contain the layout patterns of multiple identical (and adjacent) die.

After the baseline image has been provided at operation 601, the reticle is inspected to obtain a test image of the reticle or a portion of the reticle under analysis in operation 604. Any suitable mechanism may be implemented for obtaining the test image. For example, an optical or ebeam image may be obtained. In operation 606, the test image is compared to the baseline image. This comparison is based, in part, on the flagged critical regions of the provided circuit pattern database. In other words, the flagged regions indicate the type of inspection to be performed on the corresponding region of the reticle.

Figure 7:
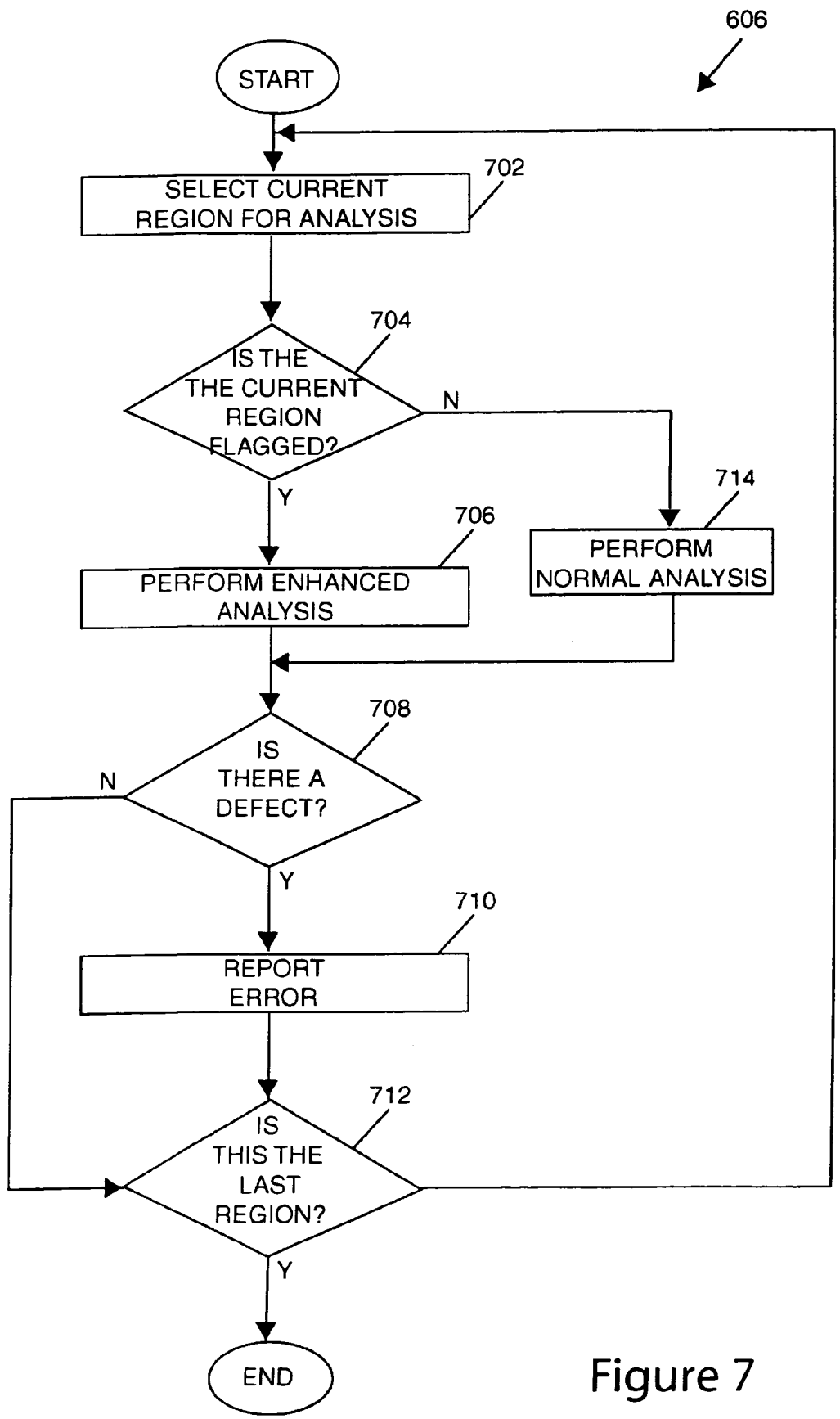
FIG. 7 is a flowchart illustrating the operation of FIG. 6 of comparing the test and baseline images in accordance with one embodiment of the present invention.

FIG. 7 is a flowchart illustrating the operation 606 of FIG. 6 of comparing the test and baseline images in accordance with one embodiment of the present invention. In operation 702, a current region of the reticle is selected for analysis. It is then determined whether the current region is flagged as a critical region in operation 704.

If the current region is flagged as a critical region, an enhanced analysis is performed on the corresponding critical region of the reticle, or representative test image, in operation 706. The enhanced analysis may also depend on the flag type. That is, different flag types may indicate different types of enhanced analysis. Otherwise, if the current region is not flagged, a normal analysis is performed in operation 714.

Each type of enhanced analysis may include any suitable type of inspection procedure for verifying whether the resulting reticle meets design specifications. In one embodiment, each enhanced analysis provides a way to inspect a sample more stringently to determine whether the corresponding critical regions meet design specifications, as opposed to a less stringent inspection of normal, nonflagged regions. For example, an edge of the critical region on the test image may be compared to an edge of the baseline image, and it is then determined whether the edge positions vary by more than an enhanced threshold. By way of another example, an enhanced analysis may include a qualitatively different analysis from the normal analysis. That is, a different inspection algorithm is used for a particular type of enhanced analysis than for the normal analysis.

A normal analysis may be in the form of any inspection procedure that is suitable for implementing on most regions of the reticle (e.g., the non-critical regions of the reticle). For example, the normal analysis may use a conventional threshold for inspecting the normal (or nonflagged) regions of the reticle. Such thresholds are typically less stringent than those employed in critical regions. In other words, some variations from the baseline that would constitute defects under enhanced analysis will not constitute defects under normal analysis. In some cases, the "normal analysis" for some particular types of reticle may actually require no inspection. That is, the reticle features in the unflagged regions may be so unimportant that they are allowed to include any number of defects. CMP markings may be one such type of feature.

Different types of types of structures, which are subject to different types of inspection or fabrication procedures, are described with respect to FIGS. 8A through 8I. Different types of flags (or the absence of a flag) may be used to indicate these different types of structures or regions thereby indicating different types of inspection or fabrication procedures to be performed thereon. In other words, different flags may indicate different types of inspection or fabrication procedures. The techniques of the present invention may include flagging one or more of these different types of regions. Also, the structures and techniques described with respect to FIGS. 8A through 8L are merely exemplary and are not meant to limit the scope of the invention.

Figure 8A:
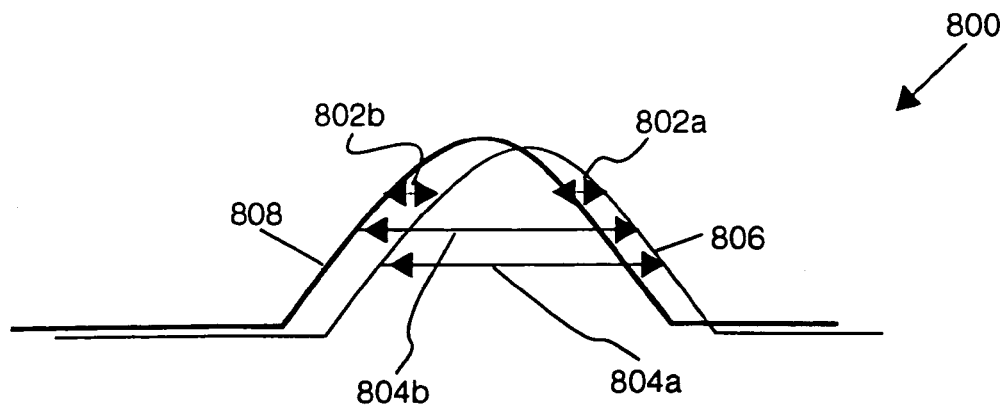
FIG. 8A is a diagram of a first example of an enhanced analysis and a normal analysis in accordance with one embodiment of the current invention.

Different test portions may be subject to an enhanced or normal analysis depending on the test regions' circuit characterization as indicated by the presence or absence of a flag. An enhanced analysis generally refers to a more stringent or thorough analysis, while a normal analysis generally refers to a less stringent or thorough analysis. FIG. 8A is a diagram of a first example of an enhanced analysis and a normal analysis in accordance with one embodiment of the current invention. As shown, a test feature 806 (i.e., a feature under analysis) is compared to a baseline feature 808. The baseline feature corresponds to expected results, and the test feature corresponds to actual results of reticle fabrication.

During a normal analysis, the test feature's edge positions are merely compared to the baseline feature's edge positions. As shown, a positive difference 802a and a negative difference 802b is calculated for the two edges. A total difference may then be calculated for the test and baseline features. In analyses, the positive and negative differences cancel each other out, so that the total difference between the feature sizes would be about equal to zero. If the design requirements specify that the test feature must not vary from the baseline feature by more than a normal threshold, the normal analysis may result in a defect that is undetected. More typically, the magnitudes of the edge position deviations are summed. In such cases, a defect would normally be found in the FIG. 8A example.

However, if some other parameter of the test feature is deemed more important than the positions of the test feature edges relative to the baseline feature edges, the feature may be flagged to indicate that a qualitatively different inspection is to be performed. For example, the feature may be flagged as a gate (see FIG. 5C) or line to indicate that an average width 804a of the feature under analysis is to be compared to an average width of the baseline feature 804b. Alternatively, the feature may be flagged to indicate that the average width of the test feature must be within a predetermined range. These comparisons and analyses might be useful when the line or gate width is far more critical than an offset in the overall positions of the lines or gates. If both the line width and overall position are important, the region could be subject to both normal analysis (edge position) and enhanced analysis (line width). In the example of FIG. 8A, a line width analysis would likely indicate that there is not a significant deviation between the baseline and current images (while the normal edge position analysis would indicate a defect).

Figure 8B:
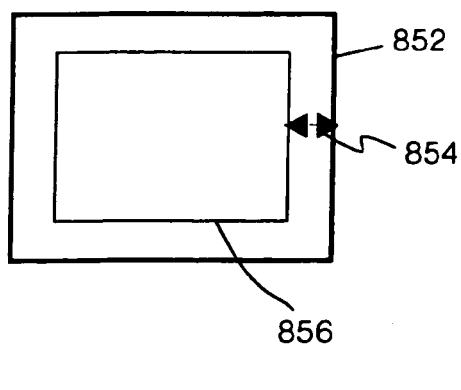
FIGS. 8B and 8C are diagrams of a second and third example of an enhanced analysis and a normal analysis in accordance with one embodiment of the current invention.
Figure 8C:
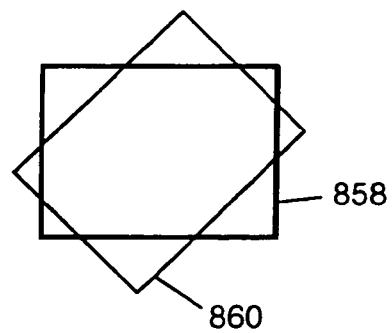

FIGS. 8B and 8C are diagrams of a second and third example of an enhanced analysis and a normal analysis in accordance with one embodiment of the current invention. As shown in FIG. 8B, a test feature 856 is compared to a baseline feature 852. During a normal inspection, as described above, edge differences (e.g. 854) are calculated between the test and baseline features. In this example, the edge differences may be relatively small or could cancel each other out even though the overall size of the test feature is significantly different from the baseline feature's overall size. In contrast, as shown in FIG. 8C, although the test feature 860 has about the same area size as the baseline feature 858, the edge differences might be relatively large and not cancel each other out under a normal analysis and, thus, the total edge differences will be significant. In sum, as shown in FIG. 8B, significant area differences may not be detected, and as shown in FIG. 8C, identical areas may result in defect detection.

In some applications, normal analysis is not adequate for inspecting certain critical features of the IC device, such as contacts. That is, the contact needs to be a certain minimum area size to accommodate a particular energy throughput, for example. Also, the particular shape of a contact is less important, as long as the area size is adequate. Accordingly, the present invention allows the baseline feature to be flagged to indicate an enhanced inspection that includes checking the area size. For example, the flag may indicate that the area of the feature under analysis is to be compared to the baseline feature's area. Thus, if the area of certain reticle features is an important design requirement, the present invention allows corresponding baseline images to be flagged as requiring an enhanced analysis that employs area comparisons.

The presence of flags (or absence of flags) may be used to indicate any suitable type of circuit characteristic of the associated flagged or non-flagged test portion. As described above with respect to FIG. 1, each differently flagged region will be subject to a different type of inspection or fabrication procedure. Now referring to FIGS. 8D–8L, embodiments of the invention where the circuit designer's intent regarding an inspection/fabrication criterion is conveyed to the inspection/fabrication system by utilizing a flag indicating a circuit characterization type will be described in detail. In the following embodiments, existence of a flag or non-existence of a flag corresponds to a circuit characterization type. The circuit characterization type is determined based on the test portion's electrical criticality of, for example, (i) a poly gate level, (ii) a contact and via hole level, (iii) a metal level, or (iv) a critical path level.

First, a method of modifying an inspection/fabrication criterion based on a circuit characterization type determined based on the test portion's electrical criticality of a poly gate level will be described referring to FIGS. 8D–8G.

FIG. 8D is a diagram of two representations of layout patterns used to fabricate a transistor according to one embodiment of the present invention. FIG. 8E is a schematic diagram of an equivalent circuit of the transistor shown in FIG. 8D. A gate area 816, a drain area 818, and a source area 820 in FIG. 8D correspond to a gate 822, a drain 824, and a source 826 in FIG. 8E, respectively.

The two representations shown in FIG. 8D provide a transistor representation 810 which includes a poly layer representation 812 representing a polysilicon layer of the transistor, and an active area representation 814 representing an active area within a semiconductor substrate. The poly layer representation 812 includes the gate area 816 of the transistor.

The active area layout pattern is indicated by dotted boundaries (i.e., the gate area 816, the drain area 818 and the source area 820) in the representation 814. The active area layout pattern 814 includes the gate area 816, the drain area 818 and the source area 820. The active area representation 814 contains no critical regions, and thus, has no flagged regions in this example.

The polysilicon layout pattern is indicated by a solid boundary in the representation 812. Residing within the solid boundary is a polysilicon strip. The polysilicon layout pattern contains a flagged critical region 816 at its gate electrode. In poly level representation 812, the critical region 816 is defined by the intersection of the poly layer representation 812 and the active area representation 814.

In the above-described example shown in FIG. 8D, the transistor representation 810 functions as an active transistor (or, an active switching device). Therefore, the transistor representation 810 has the critical region 816 flagged at its gate region. Thus, the region 816 has a flag corresponding to enhanced inspection/fabrication. In one embodiment of the present invention, a circuit extractor automatically generates a circuit characterization type of an "active transistor" corresponding to the transistor representation 810 based on the transistor representation 810 itself, or on the data representing its equivalent schematic shown in FIG. 8E. Alternatively, a human circuit designer may manually designate the transistor representation 810 as an active transistor.

In order to indicate the circuit characterization type of a specific device area, a flag representing the circuit characterization type (e.g., an active transistor, here) may be stored with the electronic data of the transistor representation 810 or may be stored separately from the electronic data of the transistor representation 810. The transistor representation 810 may include the flag indicating the circuit characterization type. An inspection/fabrication system inspects and/or fabricates a portion of the semiconductor device using an inspection/fabrication criterion. Such criteria may be modified based on existence or non-existence of the flag representing the circuit characterization type.

FIG. 8F is a diagram of two representations of layout patterns used to fabricate a decoupling capacitor according to one embodiment of the present invention. FIG. 8G is a schematic diagram of an equivalent circuit of the decoupling capacitor shown in FIG. 8F. A polysilicon area 830, and an active area 832 in FIG. 8F correspond to a first electrode 834, and a second electrode 836 of a decoupling capacitor in FIG. 8G, respectively. The first electrode 834 and the second electrode 836 of the decoupling capacitor are, for example, connected to the power supply (+VDD) and the ground (GND), respectively.

The two representations shown in FIG. 8F provide a decoupling capacitor representation 838 which includes a poly layer representation 840 (indicated by a solid boundary) representing a polysilicon layer of the capacitor, and the active area representation 832 (indicated by a dotted boundary) representing the layout of the active area on a semiconductor substrate.

Since the polysilicon area 830 (indicated by the hatched area) functions as an electrode of a decoupling capacitor (or, a decoupling transistor) which is a non-active device, the poly layer representation 840 does not have to be subject to stringent inspection/fabrication. Therefore, the polysilicon area 830 has no critical region, and thus, has no flag corresponding to enhanced inspection/fabrication. In one example implementation, a current region having a flag which indicates an active device is compared to an image of a corresponding baseline region to obtain a difference image. A lower threshold (as compared with a non-active region) is used to determine whether the difference indicates a defect. In another application, a higher resolution is used to fabricate a region that is flagged (or not flagged) as an active region, as compared with a region that is flagged (or not flagged) as a non-active region.

In one embodiment of the present invention, a circuit extractor automatically generates a circuit characterization type of a "decoupling capacitor" corresponding to the polysilicon area 830 based on the decoupling capacitor representation 838 itself, or on data representing its equivalent schematic shown in FIG. 8G. Alternatively, a human circuit designer may manually designate the polysilicon area 830 as a decoupling capacitor.

In order to indicate the circuit characterization type of a specific device area, a flag representing the circuit characterization type (e.g., a decoupling capacitor, here) may be stored with the electronic data of the decoupling capacitor representation 838 or may be stored separately from the electronic data of the decoupling capacitor representation 838. The decoupling capacitor representation 838 may include the flag indicating the circuit characterization type.

In one specific embodiment, the circuit characterization type of "1" indicates that the device is an active transistor, while the circuit characterization type of "0" indicates that the device is a decoupling capacitor. Alternatively, existence of a flag "1" may indicate that the circuit characterization type is an active transistor, while non-existence of a flag "1" may indicate that the circuit characterization type is a decoupling capacitor. Furthermore, non-existence of a flag "1" may indicate that the circuit characterization type is an active transistor, while existence of a flag "1" may indicate that the circuit characterization type is a decoupling capacitor. It should be appreciated that a specific flag actually used for indicating the circuit characterization type may be selected from any suitable machine readable symbols including alphanumeric characters and combination thereof. This flexibility of the flag for representing the circuit characterization type also applies to other circuit type examples described below referring to FIGS. 8H–8L.

Second, a method of modifying an inspection/fabrication criterion based on a circuit characterization type determined based on the test portion's electrical criticality of a contact and via hole level will be described referring to FIGS. 8H–8I.

FIG. 8H is a diagram of two representations of layout patterns used to fabricate via holes which are subject to more stringent inspection/fabrication according to one embodiment of the present invention. FIG. 8I is a diagram of two representations of layout patterns used to fabricate via holes which are subject to less stringent inspection/fabrication according to one embodiment of the present invention.

The two representations shown in FIG. 8H provide a single via hole representation 840 which includes a first metal layer representation 842 (indicated by a solid boundary), a second metal layer representation 844 (indicated by a dotted boundary), and a via hole representation 846 representing the layout of the via hole connecting the polysilicon layer and the diffusion layer.

In the example shown in FIG. 8H, the via hole representation 840 has a critical region of the via hole representation 846 since there is only a single via hole connecting the two layers 842 and 844. Since a single via hole's failure is more critical than a failure of a via within a redundant contact, the via hole representation 846 has a flag corresponding to enhanced inspection/fabrication, as compared with a redundant via hole contact. In one embodiment of the present invention, a circuit extractor automatically generates a circuit characterization type of a "single via hole area" corresponding to the via hole representation 840 based on the via hole representation 840 itself. Alternatively, a human circuit designer may manually designate the transistor representation 840 as a single via hole area.

In order to indicate the circuit characterization type of a specific device area, a flag representing the circuit characterization type (e.g., a single via hole area, here) may be stored with the electronic data of the via hole representation 840 or may be stored separately from the electronic data of the via hole representation 840. The via hole representation 840 may include the flag indicating the circuit characterization type. An inspection/fabrication system inspects and/or fabricates a portion of the semiconductor device using an inspection/fabrication criteria. Such criteria may be modified based on existence or non-existence of the flag representing the circuit characterization type. For example, a region having a flag (or no flag) indicating a single hole area may be inspected more stringently than a region having a flag (or no flag) indicating a redundant hole area. In one example implementation, an image of a current region having a flag indicating a single hole area is compared with an image of a corresponding baseline region to obtain a difference image. A lower threshold (as compared with a redundant hole area) is then used to determine whether the difference is a defect.

The two representations shown in FIG. 8I provide a multiple via hole representation 870 which includes a first metal layer representation 872 (indicated by a solid boundary), a second metal layer representation 874 (indicated by a dotted boundary), and via hole representations 876–881 representing the layout of the via holes each of which connects the first and second metal layers.

In the example shown in FIG. 8I, the via hole representation 870 has no critical regions since there are a plurality of via holes connecting the two layers 872 and 874. Even if the via hole 876 were to not function as designed, there are still five backup via holes 877–881 for connecting the two layers 872 and 874. Thus, each of the via hole representations 876–881 has a flag (or no flag) corresponding to normal inspection/fabrication. In one embodiment of the present invention, a circuit extractor automatically generates a circuit characterization type of a "multiple via hole area" corresponding to the via hole representation 870 based on the via hole representation 870 itself. Alternatively, a human circuit designer may manually designate the via hole representation 870 as a multiple via hole area.

In order to indicate the circuit characterization type of a specific device area, a flag representing the circuit characterization type (e.g., a multiple via hole area, here) may be stored with the electronic data of the via hole representation 870 or may be stored separately from the electronic data of the via hole representation 870. The via hole representation 870 may include the flag indicating the circuit characterization type. An inspection/fabrication system inspects and/or fabricates a portion of the semiconductor device using an inspection/fabrication criteria. Such criteria may be modified based on existence or non-existence of the flag representing the circuit characterization type.

In one specific embodiment, the circuit characterization type of "1" indicates that the test portion is a single via hole area, while the circuit characterization type of "0" indicates that the test portion is a multiple via hole area. Alternatively, existence of a flag "1" may indicate that the circuit characterization type is a single via hole area, while non-existence of a flag "1" may indicate that the circuit characterization type is a multiple via hole area. Furthermore, non-existence of a flag "1" may indicate that the circuit characterization type is a single via hole area, while existence of a flag "1" may indicate that the circuit characterization type is a multiple via hole area.

According to one embodiment of the invention, when a single via hole area is under inspection/fabrication, the inspection/fabrication system determines that the area has no defect only if the single via hole 846 passes the inspection/fabrication criterion. By contrast, when a multiple via hole area is under inspection/fabrication, the inspection/fabrication system determines that the area has no defect as long as at least one of the via holes 876–881 passes the inspection/fabrication criterion. Alternatively, the inspection/fabrication system determines that the area has no defect as long as a minimum number, or a minimum percentage of the via holes 876–881 pass the inspection/fabrication criterion. Thus, this specific embodiment of the invention enables the system to determine the existence of a defect based on the criticality of the contact and via hole level.

Alternatively, a flag may indicate a number of via holes which connect two layers within the test portion, and an inspection/fabrication criterion may be modified based on the flag indicating the via hole number. For example, the flag indicates "1" in case of FIG. 8H, while the flag indicates "6" in case of FIG. 8I. Thus, the system is capable of modifying the stringency of inspection/fabrication based on the flag. Specifically, the inspection/fabrication becomes more stringent as the flag decreases. For example, a gradation of threshold values may be used to inspect a gradation of different via hole numbers.

Third, a method of modifying an inspection/fabrication criterion based on a circuit characterization type determined based on the test portion's electrical criticality of a metal level will be described referring to FIG. 8J.

Figure 8J:
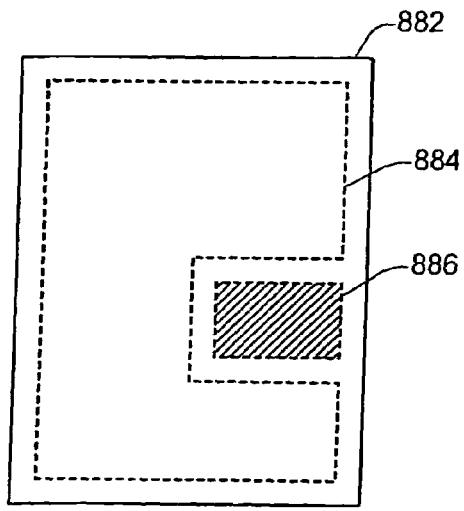
FIG. 8J is a diagram of a layout pattern used to fabricate a semiconductor device according to one embodiment of the present invention.

FIG. 8J is a diagram of a layout pattern used to fabricate a semiconductor device 882 according to one embodiment of the present invention. The semiconductor device 882 includes an active element portion 884 and a dummy element portion 886. The active element portion 884 corresponds to electrically necessary circuitry to achieve designed functionality, while the dummy element portion 886 is automatically generated by a circuit extractor software for uniform CMP (chemical mechanical polishing). In other words, devices included in the dummy element portion 886 do not have to function properly. Thus, the active element portion 884 is preferably subject to a more stringent inspection/fabrication, while the dummy element portion 886 does not (or, only has to be subject to less stringent inspection/fabrication).

Similar to the above examples described referring to FIGS. 8A–8F, according to one specific embodiment of the invention, each of the active element portion 884 and the dummy element portion 886 has a corresponding flag indicating the circuit characterization type. For example, the active element portion 884 has a flag indicating the circuit characterization type of an "active element portion," while the dummy element portion 886 has a flag indicating the circuit characterization type of a "dummy element portion." Alternatively, the active element portion 884 has a flag indicating an active element portion, while the dummy element 886 has no flag, whose absence indicates a dummy element portion.

Thus, this specific embodiment of the invention enables the inspection/fabrication system to modify an inspection/fabrication criterion based on the flag indicating the circuit characterization type. For example, a portion having a flag indicating an active element portion is subject to more stringent inspection/fabrication, while a portion having a flag indicating a dummy element portion is subject to less stringent inspection/fabrication.

Finally, a method of modifying an inspection/fabrication criterion based on a circuit characterization type representing a critical path level or symmetry will be described referring to FIGS. 8K, 8L, and 8M.

Any suitable type of critical path may be characterized to determine an inspection or fabrication criterion. FIG. 8K is a diagram of a layout pattern used to fabricate a semiconductor device 890 including a pair of transistors according to one embodiment of the present invention. FIG. 8L is a schematic diagram of an equivalent circuit of the semiconductor device 890 shown in FIG. 8K. The semiconductor device 890 includes a poly layer representations 892 and 896 (indicated by a solid boundary), and an active area representation 899 (indicated by dotted boundaries). The poly layer representations 892 and 896 include gate regions 894 and 898, respectively. The gate regions 894 and 898 in FIG. 8K correspond to gates 894 and 898 of the pair of the transistors shown in FIG. 8L.

Figure 8K:
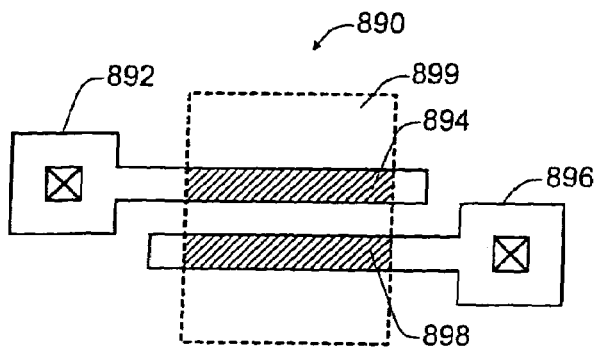
FIG. 8K is a diagram of a layout pattern used to fabricate a semiconductor device including a pair of transistors according to one embodiment of the present invention.
Figure 8L:
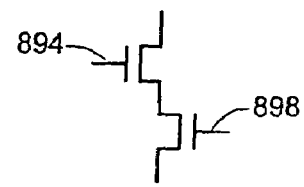
FIG. 8L is a schematic diagram of an equivalent circuit of the semiconductor device shown in FIG. 8K.

The semiconductor device 890 shown in FIGS. 8K and 8L has a critical path. In this example, a gate CD (critical dimension) should be controlled since the gate regions 894 and 898 are critical to the operation of the device 890. Thus, the gate regions 894 and 898 (indicated by a hatched portion) are considered as critical paths since the critical dimension of the gate regions 894 and 898 determine the characteristics of the device. Therefore, the gate regions 894 and 898 are critical regions which need to be examined more thoroughly. In one specific embodiment of the present invention, a flag indicating a circuit characterization type of a "critical path" and a flag indicating a circuit characterization type of a "non-critical path" may be added to the electronic data of the semiconductor device 890.

For example, a portion having a flag indicating a circuit characterization type of a critical path is subject to a more stringent inspection/fabrication process compared to one without such a flag. Such a flag indicating a circuit characterization type of a critical path may be added to a device used in a PLL (phase locked loop), a clock timing unit, and other timing-critical circuitry.

Figure 8M:
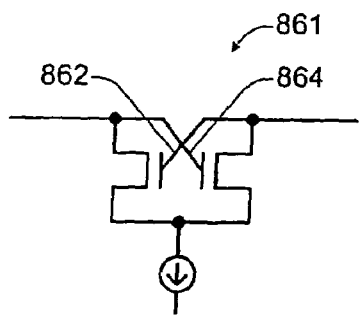
FIG. 8M is a schematic diagram of an equivalent circuit of a semiconductor device for which one embodiment of the present invention may be used.

The semiconductor device 861 shown in FIG. 8M could be used for a sense amplifier. In this example, the timing of the gate regions 862 and 864 is critical to the operation of the sense amplifier. Thus, the gate regions 862 and 864 are considered as being critical portions since the two transistors should match exactly in geometry (especially, the gate regions 862 and 864), which determines the characteristics of the sense amplifier 861. In other words, the two transistors included in the device 861 require more precise symmetry. Therefore, the gate regions 862 and 864 are critical regions which need to be examined more thoroughly. In one specific embodiment of the present invention, a flag indicating a circuit characterization type of a "symmetry-critical portion" and a flag indicating a circuit characterization type of a "non-symmetry-critical portion" may be added to the electronic data of the semiconductor device 861.

In this specification, various geometric patterns of a device which are illustrated in, for example, FIGS. 2, 4, 8D, 8F, and 8H–8K may be represented by "electronic representation" including any suitable one or more formats, codes, symbols, or combination of thereof. Further, such electronic representation may be stored in any suitable electronic device, and be transmitted by any suitable medium.

Turning back to FIG. 7, after analysis is complete for the current region, it is then determined whether there is a defect in operation 708 (e.g., the edge position, area, or line width deviation between the baseline and current images is greater than a defined threshold). Different thresholds may be used for differently flagged and thereby differently characterized regions. If there is a defect, an error report may be generated in operation 710. It is then determined whether there are any more regions to inspect in operation 712. If there are more regions to inspect, a new current region is obtained in operation 702 and analyzed. Otherwise, if there are no more regions, the process 606 ends.

Figure 9:
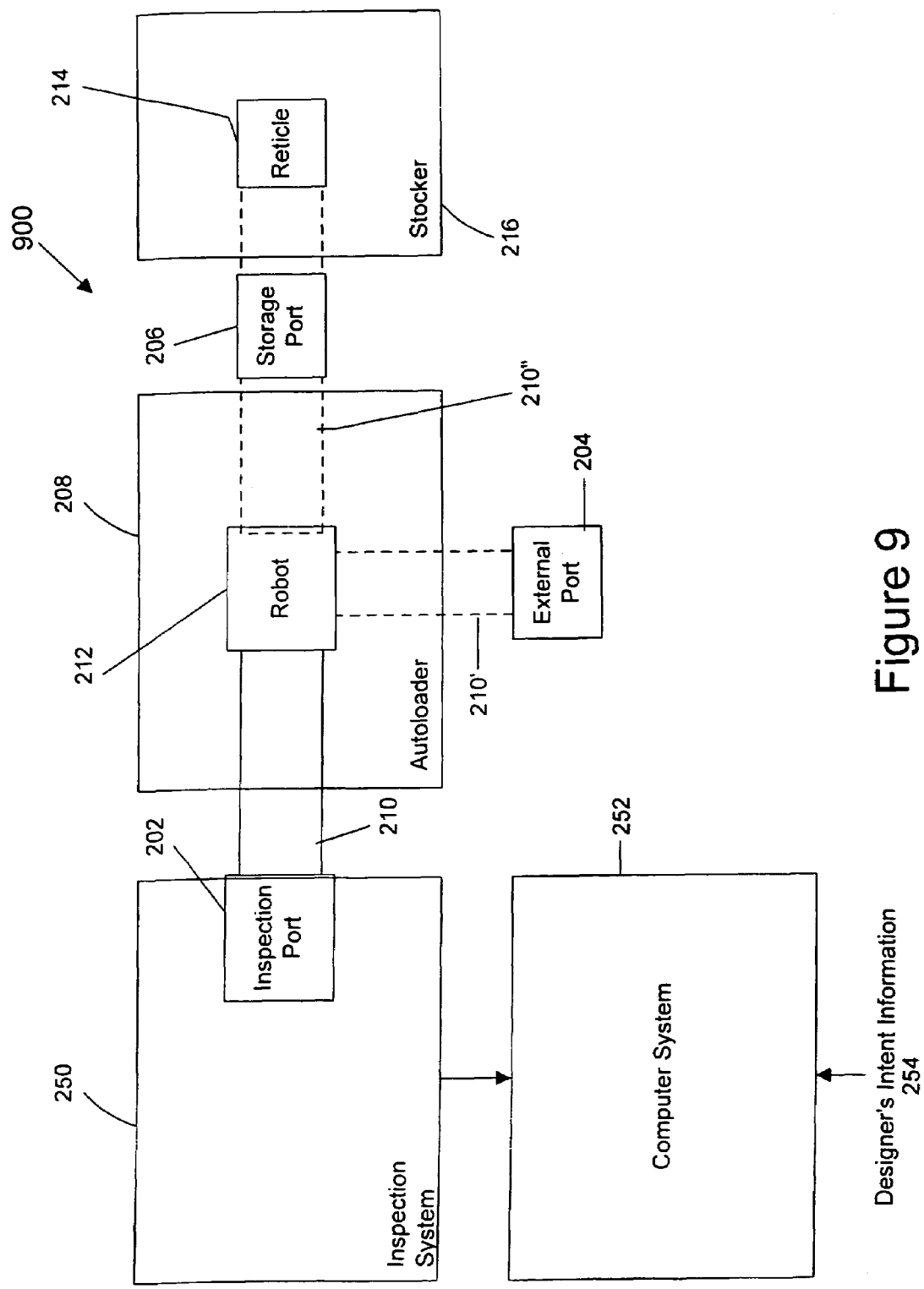
FIG. 9 shows a reticle inspection station-reticle stocker station upon which process of FIG. 6 of inspecting the reticle would be implemented in a preferred embodiment of the present invention.

The invention may be used with any suitable inspection or fabrication system. FIG. 9 shows a reticle inspection station-reticle stocker station 900 where process 108 of FIG. 6 would be implemented in a preferred embodiment of the present invention. An autoloader 208 for automatically transporting reticles includes a robot 212 having an arm 210 extending towards a inspection port 202 of a reticle inspection station 250. Arm 210 may rotate and can extend towards an external port 204 when in its state denoted by reference number 210'. Similarly, when in its state denoted by reference number 210", the robotic arm can also extend towards a storage port 206 of a reticle stocker station 216 that typically includes several slots or tracks for storing reticles. The robotic arm is designed to further extend and retrieve a reticle 214 from reticle stocker station 216.

A typical inspection process, according to one embodiment of the present invention, may begin after reticle 214 is placed on external port 204, with the intention of storing the reticle in reticle stocker station 216 until it is used in a subsequent inspection application, for example. Robotic arm in its position 210' transports the reticle from external port 204 and stores it in a loading port of reticle stocker station 216 by extending as shown in FIG. 9. When the reticle is needed for production, for example, robotic arm 210" retrieves reticle 214 from the loading port and places it on inspection port 202 of inspection system 250.

The inspection system 250 is coupled with a computer system 252 where inspection process 108 of FIG. 6 detailed above is carried out and it is determined whether the reticle has passed inspection. The computer system 252 may be integral to inspection system 250 or separate from the inspection system 250. The inspection system 250 receives data 254 regarding the designer's intent in the form of data structures, for example, having flags for regions that require special inspection. Additionally, the computer system 252 receives image data from the inspection system 250. The image data is analyzed based, at least in part, on the user's design intent data 254. After the reticle inspection has concluded, reticle 214 is placed on external port 204 so that it may be carried to a fabrication facility for use, assuming of course, that it has passed inspection. Alternatively, the reticle 214 may be repaired or remade.

Suitable computer systems for use in implementing and controlling the methods in the present invention (e.g., controlling the settings of the various scanning apparatus components, retrieving database records specifying regions of normal and enhanced analysis, storing baseline image of the reticle, storing a new image of the reticle, comparing the new image with the baseline image, storing the location of defects, etc.) may be obtained from various vendors. In one preferred embodiment, an appropriately programmed Silicon Graphics 0-200 computer (Mountain View, Calif.) or Sun SPARC (Sun Microsystems, Sunnyvale, Calif.) may be employed. In any case, the computer system preferably has one or more processors coupled to input/output ports, and one or more memories via appropriate buses or other communication mechanisms.

The term "electronic representation" as used herein covers any machine readable representation. Typically, such representations are stored on magnetic, electronic, or optically readable media. The content of such representations may be transmitted as electrical signals, magnetic signals, electromagnetic signals, optical signals, etc.

Preferably, an optical, electron beam, or other inspection system is integrated with a computer system which implements many of the method steps of this invention. Such composite system preferably includes at least (a) a baseline image (preferably compacted) stored in a memory, (b) an imaging system arranged to generate an optical or electron beam image of the reticle, and (c) a processing unit configured to compare the baseline and current test images and thereby identify defects. At a minimum, the imaging system will usually include (i) a source of illumination oriented to direct radiation onto a specified location of the reticle; and (ii) one or more detectors oriented to detect an image of the reticle from the source which has been scattered by the reticle. The imaging system may also include a scanning means.

According to the various embodiments of the present invention, a reticle or integrated circuit is fabricated by utilizing two different fabrication parameter values based on the flag associated with the portion. In such an embodiment, the different fabrication parameter values may correspond to two different photolithography resolution values. Further, in the embodiment, a reticle or integrated circuit is fabricated based on the layout pattern, and the reticle or integrated circuit is inspected by utilizing two different stringency threshold values based on the flag.

It should be appreciated that a flag indicating the circuit characterization type may be assigned to a whole region of a functional element (e.g., a transistor, a capacitor) in an integrated circuit. Alternatively, such a flag may cover only a specific portion of the functional element (e.g., a gate of a transistor, an electrode of a capacitor).

A system according to the present invention may modify its inspection/fabrication criterion by combination of (i) a flag indicating the circuit characterization type (e.g., a poly gate level, a contact and via hole level, a metal level, or a critical path level), and (ii) a flag indicating other circuit attributes (e.g., a gate, a drain, a source, a power line, a ground line, and the like).

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. For example, critical areas of the circuit pattern may be flagged by providing tags within a corresponding schematic netlist or database, and the schematic database is then used to inspect the reticle.

By way of another example, regions may be flagged to indicate a less stringent or no inspection (e.g., for the noncritical CMP layer). Additionally, the regions may be flagged to indicate an extra inspection analysis, in addition to a normal analysis that is performed on both the unflagged and flagged regions.

Furthermore, the methods and apparatus described above in connection with reticle writing and inspection may be utilized in defect review, defect repair, and inspection and review of wafers produced by reticles, or wafers which are written directly without a reticle.

Accordingly, the present embodiments are to be considered as illustrative and not restrictive, and the invention is not to be limited to the details given herein, but may be modified within the scope and equivalents of the appended claims.

What is claimed is:

1. A circuit design for use with electronic design automation (EDA) tools in designing integrated circuits, the circuit design being stored on a computer readable medium and containing an electronic representation of a layout pattern for at least one layer of the circuit design on an integrated circuit, the layout pattern comprising:
    a first layout region having a first flag associated therewith, the first layout region corresponding to a first procedure region on a reticle or an integrated circuit; and
    a second layout region having a second flag or no flag associated therewith, the second layout region corresponding to a second procedure region on the reticle or the integrated circuit; wherein
    the first flag of the first layout region is readable by an inspection or a fabrication system, and indicates that the first procedure region of the reticle or the integrated circuit has a first circuit characterization type and is thereby subject to a first inspection or fabrication procedure that is to be performed on the first procedure region on the reticle or the integrated circuit;
    the second flag or absence of a flag of the second layout region is readable by the inspection or the fabrication system, and indicates that the second procedure region of the reticle or integrated circuit has a second circuit characterization type and is thereby subject to a second inspection or fabrication procedure that is to be performed on the second procedure region on the reticle or the integrated circuit;
    the second inspection or fabrication procedure differs from the first inspection or fabrication procedure; and
    the first circuit characterization type and the second circuit characterization type identify types of structures of the first and second layout regions,
    wherein the first circuit characterization type is an active transistor, and the second circuit characterization type is a decoupling transistor.

2. A circuit design for use with electronic design automation (EDA) tools in designing integrated circuits, the circuit design being stored on a computer readable medium and containing an electronic representation of a layout pattern for at least one layer of the circuit design on an integrated circuit, the layout pattern comprising:
    a first layout region having a first flag associated therewith, the first layout region corresponding to a first procedure region on a reticle or an integrated circuit; and
    a second layout region having a second flag or no flag associated therewith, the second layout region corresponding to a second procedure region on the reticle or the integrated circuit; wherein
    the first flag of the first layout region is readable by an inspection or a fabrication system, and indicates that the first procedure region of the reticle or the integrated circuit has a first circuit characterization type and is thereby subject to a first inspection or fabrication procedure that is to be performed on the first procedure region on the reticle or the integrated circuit;
    the second flag or absence of a flag of the second layout region is readable by the inspection or the fabrication system, and indicates that the second procedure region of the reticle or integrated circuit has a second circuit characterization type and is thereby subject to a second inspection or fabrication procedure that is to be performed on the second procedure region on the reticle or the integrated circuit;
    the second inspection or fabrication procedure differs from the first inspection or fabrication procedure; and
    the first circuit characterization type and the second circuit characterization type identify types of structures of the first and second layout regions,
    wherein the first circuit characterization type is an active element, and the second circuit characterization type is a dummy element.

3. A method of inspecting a reticle for defining a circuit layer pattern, the method comprising:
    analyzing the circuit layer pattern to obtain a circuit characterization;
    categorizing an area of the reticle into a first region and a second region based on the circuit characterization;
    providing a test reticle image of the reticle;
    providing a baseline representation containing an expected pattern of the test reticle image;
    comparing the first region of the test reticle image to the first region of the baseline representation by a first analysis; and
    comparing the second region of the test reticle image to the second region of the baseline representation by a second analysis; wherein
    the first analysis differs from the second analysis and this difference is based on categorization of the first and second regions; and
    the circuit characterization identifies types of structures of the first and second layout regions,
    wherein the circuit characterization is a function of a transistor included in the area, and
    wherein the function of the transistor is a decoupling capacitor.

4. A method of inspecting a reticle for defining a circuit layer pattern, the method comprising:

analyzing the circuit layer pattern to obtain a circuit characterization;

categorizing an area of the reticle into a first region and a second region based on the circuit characterization;

providing a test reticle image of the reticle;

providing a baseline representation containing an expected pattern of the test reticle image;

comparing the first region of the test reticle image to the first region of the baseline representation by a first analysis;

comparing the second region of the test reticle image to the second region of the baseline representation by a second analysis; and adding a flag identifying whether the circuit layer pattern is a single via area or a multiple via area to the circuit layer pattern based on a number of via holes, wherein the first analysis differs from the second analysis and this difference is based on the flag.

5. A method of generating a layout pattern with a flag for an integrated circuit device, comprising:

generating at least one of a schematic representation and a high level description of the integrated circuit device;

generating the layout pattern based on the at least one of the schematic representation and the high level description; and adding the flag identifying whether the layout pattern is a single via area or a multiple via area to the layout pattern based on a number of via holes.

* * * * *